United States Patent [19]
Walt et al.

[11] Patent Number: 5,814,524
[45] Date of Patent: Sep. 29, 1998

[54] OPTICAL SENSOR APPARATUS FOR FAR-FIELD VIEWING AND MAKING OPTICAL ANALYTICAL MEASUREMENTS AT REMOTE LOCATIONS

[75] Inventors: David R. Walt, Lexington; Karri L Michael, Somerville; Suneet Chadha, Melrose, all of Mass.

[73] Assignee: Trustees of Tufts College, Medford, Mass.

[21] Appl. No.: 572,005

[22] Filed: Dec. 14, 1995

[51] Int. Cl.$^6$ .................. G01N 33/543; G01N 33/552
[52] U.S. Cl. .................. 436/518; 385/12; 385/115; 385/123; 422/55; 422/57; 422/58; 422/82.05; 422/82.07; 422/82.08; 422/82.09; 422/82.11; 435/287.1; 435/287.2; 435/288.7; 435/808; 436/164; 436/165; 436/172; 436/527; 436/800; 436/805
[58] Field of Search .................. 385/12, 115, 123; 422/55, 57, 58, 82.05–82.09, 82.11; 435/287.1, 287.2, 288.7, 808; 436/164, 165, 172, 518, 527, 800, 805

[56] References Cited

U.S. PATENT DOCUMENTS

| | | |
|---|---|---|
| 5,244,636 | 9/1993 | Walt et al. .................. 422/82.07 |
| 5,244,813 | 9/1993 | Walt et al. .................. 436/172 |
| 5,298,741 | 3/1994 | Walt et al. .................. 422/82.07 |
| 5,320,814 | 6/1994 | Walt et al. .................. 422/82.07 |

Primary Examiner—Christopher L. Chin
Attorney, Agent, or Firm—R. Dennis Creehan

[57] ABSTRACT

The present invention is an optical sensor apparatus for far-field viewing and imaging as well as for the optical detection and analytical measurement of at least one species of analyte in a remotely-positioned fluid sample. The apparatus employs an imaging fiber comprising a fiber optic array and a Gradient Index lens; and utilizes a remotely-positioned solid substrate having light energy absorbing indicator ligands on an external surface for reactive contact with individual species of analytes when present in a fluid sample. The optical sensor apparatus is able to view an object and provide an image of the object located at a pre-set optical distance remote from the imaging fiber. The apparatus is also able to detect and identify, qualitatively and quantitatively, one or more analytes of interest in a flowing solid, gaseous, or liquid sample at remote locations distanced from the imaging fiber itself.

12 Claims, 9 Drawing Sheets

OPTICAL SENSOR APPARATUS FOR FAR-FIELD VIEWING AND MAKING OPTICAL ANALYTICAL MEASUREMENTS AT REMOTE LOCATIONS

RESEARCH SUPPORT

The research for the present invention was supported by Contract Number GM48142 granted by the National Institutes Of Health. The Federal Government has certain rights in this invention.

FIELD OF THE INVENTION

The present application is concerned with fiber optic sensors and light absorbing dyes which in combination are employed for qualitative and quantitative analytical measurements and determinations; and is specifically directed to the assembly and use of a fiber optic apparatus for the detection either of a single analyte or of multiple species of analytes concurrently in a fluid sample.

BACKGROUND OF THE INVENTION

The use of optical fiber strands and fiber optic arrays, alone and in combination with light energy absorbing dyes, has rapidly evolved for imaging and for biochemical and chemical analytical determinations, particularly within the last decade. The use of optical fibers for such purposes and techniques is described by Milanovich et. al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators And Fiber Optics" in *C.R.C. Critical Reviews In Analytical Chemistry*, Vol. 19, 1988, pp.135–173; Wolfbeis, O. S., "Fiber Optic Fluorosensors In Analytical Chemistry" in *Molecular Luminescence Spectroscopy, Methods And Applications* (S. G. Schulman, editor) Wiley & Sons, New York (1988); Angel, S. M., *Spectroscopy* 2(4):38 (1987); and Walt et.al., "Chemical Sensors and Microinstrumentation", *ACS Symposium Series,* volume 493, 1989, p. 252; *Fiber Optical Chemical Sensors And Biosensors,* (O. S. Wolfbeis, editor), CRC: Boca Raton, Fla., vol. 2, 1991, pp. 267–300; *Biosensors With Fiber Optics,* Humana, Clifton, N.J., 1991.

Optical fiber strands typically are glass or plastic extended rods having a small cross-sectional diameter. When light energy is projected into one end of the fiber strand (conventionally termed the "proximal end"), the angles at which the various light energy rays strike the surface are greater than the critical angle; and such rays are "piped" through the strand's length by successive internal reflections and eventually exit from the opposite end of the strand (conventionally termed the "distal end"). Typically, bundles of these optical fiber strands are used collectively as optical imaging arrays in a variety of different applications.

For making an optical fiber into a chemical sensor, one or more light energy absorbing dyes are typically attached to the distal end of the optical fiber strand. The chemical sensor can then be used for both in-vitro and/or in-vivo applications. As used herein, light energy is photoenergy and is defined as electromagnetic radiation of any wavelength. Accordingly, the terms "light energy" and "photoenergy" include infrared, visible, and ultraviolet wavelengths conventionally employed in most optical instruments and apparatus; the term also includes the other spectral regions of X-ray and microwave wavelengths (although these are generally not used in conjunction with optical fibers).

Many of the recent improvements employing optical fiber sensors in both qualitative and quantitative analytical determinations concern the desirability of depositing and/or immobilizing various light absorbing dyes at the intended distal end of an optical fiber. For this purpose, a variety of different optical fiber chemical sensors and methods have been reported for specific analytical determinations and applications such as pH measurement, oxygen detection, and carbon dioxide analyses. The developments are exemplified by the following publications: Freeman et. al., *Anal. Chem.* 53:98 (1983); Lippitsch et. al., *Anal. Chem. Acta.* 205: 1 (1988); Wolfbeis et. al.,*Anal. Chem.* 60:2028 (1988); Jordan et. al., *Anal. Chem.* 59:437 (1987); Lubbers et. al., *Sens. Actuators* (1983); Munkholm et. al., *Anal. Chem.* 58:1427 (1986); Seitz, W. R. *Anal. Chem.* 56:16A–34A (1984); Peterson et. al., *Anal. Chem.* 52:864 (1980); Saari et. al., *Anal. Chem.* 54:821 (1982); Saari et. al.,*Anal. Chem.* 55:667 (1983); Zhujun et. al., *Anal. Chem.* 56:2199 (1984); Collison, M. E. and M. E. Meyerhoff,*Anal. Chem.* 62:425A (1990); Demas, O. N. and B. A. DeGraff, *Anal. Chem.* 63:809A (1991); Seitz, W. R., *CRC Crit. Rev. Anal. Ehem.* 19:135 (1988); Kopelman et. al., *Science* 258:778 (1992); Janata, J., *Anal. Chem.* 64:196R (1992); and Orella et. al., *Anal. Chem.* 64:2210 (1992); Janata, J., *Anal. Chem.,* 66:207R (1994); Cohen, C. B., *Anal Chem.* 65:169 (1993); Pantano et. al., P., *Anal. Chem.* 67:481A–487A (1995); Rozenzweig, Z.,*Anal. Chem.* 67:2650 (1995); Kor, S.,*Anal. Chem.* 64:2438 (1992); Wong, A., *Anal. Chem.* 64:1051 (1992); (Uttamlal, M., *Biotechnology* 13:597 (1995); Barnard, S., *Nature* 353:338 (1991); Bronk, *Anal. Chem.* 66:3519 (1994); and Bronk et. al., *Anal. Chem.* 67:2750 (1995). See also U.S. Pat. Nos. 4,822,746; 4,144,452; 4,495, 293; 5,143,853; 5,244,636; 5,244,813; 5,250,264; 5,252, 494; 5,254,477; 5,298,741; and the references cited within each of the issued patents.

Moreover, in view of the microcircuitry and CCD cameras presently available, a variety of light image processing and analytical systems have come into existence in order to enhance, analyze and mathematically process the light energies introduced to and emerging from the absorbing dyes in such optical analytical techniques. Typically, these systems provide components for image capture; data acquisition; data processing and analysis; and visual presentation to the user. Commercially available systems include the InCa$^{++}$ system from Intracellular Imaging, Inc. (Cincinnati, Ohio) and the Videometric 150 system from Oncor, Inc. (Gaitheasburg, Md.). Other conventionally available systems include the QX-7 image processing and analysis system sold by Quantex, Inc. (Sunnydal, Calif.); and the 1M Spectrofluorescence imaging system offered by SPEX Industries, Inc. (Edison, N.J.). Each of these systems may be combined with microscopes, cameras, and/or television monitors for automatic processing of all light energy determinations.

Typically, light from an appropriate energy source is used to illuminate what is chosen to be the proximal end of an optical fiber strand or a fiber bundle. The light propagates along the length of the optical fiber; and a portion of this propagated light energy exits the distal end of the optical fiber as excitation light and is absorbed at least in part by one or more light energy absorbing dyes which are used as indicators for detection purposes. After the light energy has been at least partially absorbed by the indicator dye, some light energy of varying wavelength and intensity typically returns through the distal end of the optical fiber and is conveyed through either the same fiber or a collection fiber on fibers to a detection system where the emerging light energy is observed and measured. The interaction between the exciting light energy conveyed by the optical fiber and the singular properties of the indicator light absorbing dye(s)—in the presence of a fluid sample containing one or more species of analyte as well as in the absence of any analytes of interest whatsoever—provides an optical basis for making both qualitative measurements and quantitative determinations.

Of the many different classes of light absorbing dyes which conventionally are employed as reactive indicator ligands with bundles of fiber strands and optical fibers for different analytical purposes are those compositions which emit light energy after absorption, termed "fluorophores"; and those which absorb light energy and internally convert the absorbed light energy rather than emit it as light, termed "chromophores." Fluorophores and fluorescent detection methods employing optical fibers are recognized as being markedly different and distinguishable from light energy absorbence and absorption spectroscopy.

Fluorescence is a physical phenomenon based upon the ability of some molecules to absorb light energy (photons) at specified wavelengths and then emit light energy of a longer wavelength and at a lower energy. Such emissions are called fluorescence if the emission is relatively long-lived, typically $10^{-11}$ to $10^{-7}$ seconds. Indicator substances able to fluoresce share and display a number of common characteristics: the ability to absorb light energy at a first wavelength or frequency; and to reach an excited energy state; and subsequently to emit light at a second light frequency and energy level. The absorption and fluorescence emission spectra are thus individual for each fluorophore; and are often graphically represented as two separate curves which are slightly overlapping. All fluorophores demonstrate the Stokes' shift—that is, the emitted light is always at a longer wavelength (and at a lower energy level) relative to the wavelength (and energy level) of the excitation light absorbed by the substance. Moreover, the same fluorescence emission spectrum is generally observed irrespective of the wavelength of the excitation light and, accordingly, the wavelength and energy of the excitation light may be varied within limits; but the light emitted by the fluorophore will always provide the same emission spectrum as emerging light of a different wavelength. Finally, fluorescence may be measured as the quantum yield of light emitted. The fluorescence quantum yield is the ratio of the number of photons emitted in comparison to the number of photons initially absorbed by the fluorophore. For more detailed information regarding each of these characteristics the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, Vol. 77, Wiley & Sons, Inc., 1985; *The Theory of Luminescence*, Stepanov and Gribkovskii, Iliffe Books, Ltd., London, 1968.

In comparison, indicator ligand substances which absorb light energy (and do not fluoresce) usually convert the excitation light energy into heat or kinetic energy. The ability to internally convert the absorbed light energy identifies the dye ligand as a "chromophore." Dyes used as indicators to detect the presence and/or absence of an analyte species and which absorb light energy as chromophores—do so at individual wavelengths of excitation energy and are characterized by a distinctive molar absorption coefficient at that wavelength. Chemical analyses employing fiber optic strands and absorption spectroscopy using visible and ultraviolet light wavelengths in combination with the absorption coefficient allow for the determination of concentration for specific analytes of interest by spectral measurement. The most common use of absorbance measurement via optical fibers is to determine concentration, which is calculated in accordance with Beers' law; accordingly, at a single absorbance wavelength, the greater the quantity of the composition which absorbs light energy at a given photo wavelength, the greater the optical density for the sample. In this way, the total quantity of the composition in the sample.

Nevertheless, despite the many innovations and developments in this field, and without regard to whether the apparatus is intended for in-vitro or in-vivo use, it has been impossible to both view the sample (and the surrounding environment) and concurrently to measure and detect a ligand or analyte of interest in a fluid sample using a single-core optical fiber as a sensor. Conventionally, chemical optical sensors are usually single fibers, thereby precluding their use for imaging. On the other hand, fiber optic bundles and arrays have been traditionally employed only for their original purpose—viewing or imaging. Thus, if imaging or observation is desired, a separate optical fiber strand or fiber bundle array which is unencumbered and unobscured by indicator dye reactants would be required in addition to those employed as chemical sensors in order to see the sample and its immediate surroundings directly.

In addition, two alternative modes for viewing or imaging an object using optical fibers are known: Near-field viewing; and far-field viewing. Near-field viewing is conventionally recognized and defined as an optical method having a limited region for observation and providing a sub-wavelength light energy image representation of objects only a few microns distance (typically 1–10 microns) from distal end face of the optical strand or from the distal array surface of the fiber optic array. Near-field viewing is typically performed as an optical technique without any optical aides or use of a focusing lens. Alternatively, far-field viewing is conventionally recognized and defined as an optical method using a focused distance for direct observation and clear visualization of items or objects beyond the near-field region and extending forward up to several centimeters (typically up to about 3–4 centimeters) distance from the distal optic array surface. Moreover, far-field viewing typically requires the presence and rigid attachment of a focusing objective lens (such as a gradient index lens or "GRIN" lens) to the distal array surface of the unitary fiber optic array.

Accordingly, were an improved optical apparatus developed which is able to provide for far-field viewing and for detection of at least one species of analyte in a remotely-situated fluid sample, this optical apparatus would be recognized in this field as a major advance and substantive improvement over conventionally known devices and systems. Moreover, if such an improved optical apparatus were able to provide an imaging fiber having the capability for both far-field viewing and the detection of multiple analytes of interest concurrently in a fluid sample found only at a set distance from the optical fiber, this extraordinary capability would meet and satisfy a long standing need and well recognized deficiency in this technical field.

SUMMARY OF THE INVENTION

The present invention has multiple formats and embodiments. A preferred format for the invention provides an optical apparatus for far-field detection of multiple analytes of interest in a remotely-situated fluid sample, the detection of each species of analyte being correlatable with an individual far-field optical determination, said detection apparatus comprising:

a far-field imaging fiber comprised of (a) a preformed, unitary fiber optic array comprising a plurality of individually clad, fiber optical strands disposed co-axially along their lengths and being of predetermined configuration and dimensions, said preformed unitary fiber optic array having two discrete optic array ends each of which is formed of multiple strand end faces and presents a discrete optic array surface for introduction and conveyance of light energy, and (b) a gradient index lens joined to and optically aligned with an optic array end of said unitary fiber optic array for far-field viewing of an object located within a predetermined range of optical distances from said lens;

a remotely-positioned solid substrate spaced apart from but lying within said predetermined range of optical distances from said imaging fiber, said solid substrate providing at least one discrete reaction surface in alignment with and suitable for far-field viewing via said imaging fiber;

a plurality of light energy absorbing indicator ligands disposed individually at different spatial locations on said discrete reaction surface of said remotely-positioned solid substrate, at least one of said indicator ligands reacting with an individual species of analyte when present in a fluid sample;

means for placing a fluid sample into reactive contact with said plurality of light energy absorbing indicator ligands on said reaction surface of said remotely-positioned solid substrate;

means for introducing excitation light energy of predetermined wavelength to at least one of said plurality of light energy absorbing dyes indicator ligands on said reaction surface of said remotely-positioned solid substrate; and means for detecting light energy emerging from at least one of said indicator ligands on said reaction surface of said remotely-positioned solid substrate which has been introduced to and collected by said far-field imaging fiber, each detected emerging light energy individually serving as a measure for determining at least one species of analyte in the fluid sample.

BRIEF DESCRIPTION OF THE FIGURES

The present invention may be more completely and easily understood when taken in conjunction with the accompanying drawing, in which.

DETAILED DESCRIPTION OF THE INVENTION

Figure 1:
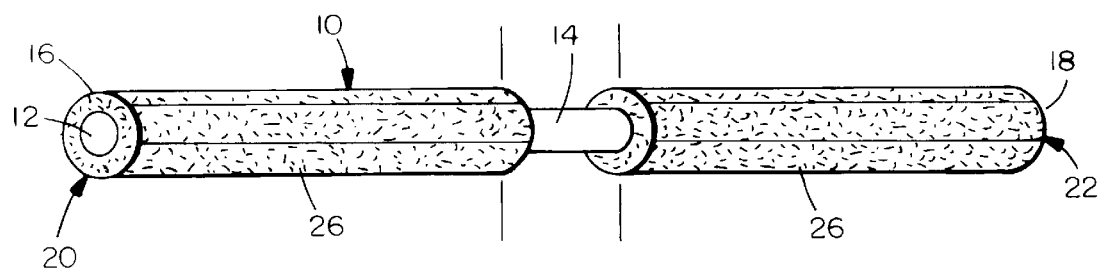
FIG. 1 is an overhead view of an individually clad, single core, fiber optical strand.

The present invention is an optical apparatus able to provide both far-field viewing as well as optical detection and analytical measurement of at least one analyte species in a fluid sample (i.e., a flowing solid, a liquid, or a gas) which is spatially removed and remote from the user. The invention thus provides for qualitative and quantitative analytical measurements and the capability of viewing and imaging the fluid test sample at a distance from the site where the optical determinations are actually performed. The optical apparatus and the system of qualitative and quantitative optical detections are based and rely upon the existence and use of a fiber optic array and GRIN lens in combination as an essential component.

Although the apparatus and the manner of using the invention may bear a superficial similarity to conventionally known optical systems for making analytical determinations, it will be recognized and appreciated that the present invention provides multiple benefits and major advantages not previously available heretofore. These include the following:

1. A fully constructed fiber optic sensor apparatus utilizes an imaging fiber comprised of a pre-formed unitary fiber optic array composed of multiple optical strands disposed co-axially along their lengths; and an optically matched micro Gradient Index ("GRIN") lens. The resulting imaging fiber allows for far-field viewing of objects or items disposed within a pre-determined range of optical distances from the GRIN lens; and provides for optical images as well as analytical measurements simultaneously or concurrently.

2. The fiber optic imaging sensor of the present invention, via the GRIN lens optically matched to a fiber optic array, provides for a greatly expanded field of view; is able to observe and image an object from a remote setting or plane; and to demagnify the image onto the optical surface of the lens. In this manner, therefore, the object being viewed is not to be in direct contact with the imaging fiber, but instead lies remote from the imaging fiber within a pre-set range of distances. In addition, the object being imaged can be far larger in diameter than the imaging fiber itself; and allows the use of a multiple analyte reaction substrate which is also markedly greater in size.

3. The present invention utilizes a remotely-positioned reaction substrate which is spaced apart but is aligned with and lies within the pre-determined range of optical distances from the imaging fiber. At least one light energy absorbing dye indicator is immobilized on a discrete reaction surface of the remotely positioned solid substrate; and the solid substrate provides a reaction surface for each of the dye-polymer formulations disposed upon it which serve as individual chemical sensing zones. The dye indicators may react either completely specifically or semi-selectively with each species of analyte to be detected; and the spectral characteristics and changes after interaction with the immobilized dye-polymer indicator sensing zones with the test sample will provide both optical determinations and analytical measurements which will detect the presence or absence of an analyte species of interest in the test sample.

4. The remotely position solid substrate of the present invention can be automated to present a range and variety of different reaction surfaces, each having an individual set of dye indicators disposed on the reaction surface. These alternative reaction surfaces can be interchanged automatically or at will to satisfy a particular use or application. Such automated interchange of multiple reaction surfaces presenting different dye indicators for reactions is very desirable for use—as for example, in microchip technology employed with capillary electrophoresis separations or DNA sequencing.

5. The present invention is especially easy to fabricate and assemble. All of the component parts are durable; are easily positioned and aligned; and provide both accuracy and precision of optical determination. Moreover, this optical sensing apparatus eliminates the need for fabrication of multiple single-analyte sensors as is conventionally performed today.

6. The optical apparatus and sensing system provides for small size of equipment; offers an insensitivity to electrical interference; and eliminates the need for a reference sensor in order to make an optical determination or measurement. The present invention is suitable and desirable for use in remote-situation applications because not only does the optical apparatus offer a field of view increased by at least one order of magnitude, but the invention also allows and envisions that the remotely positioned reaction substrates can be interchanged manually or automated at will or as necessary to extend usage and optical measurements for many different classes and species of analytes using the same imaging fiber-GRIN sensor system.

7. The optical sensor apparatus of the present invention can be utilized and applied for quantitative and/or qualitative measurements; be used in remote site locations for chemical, clinical, and environmental chemical sensing and monitoring; and is suitable for the testing of any fluid sample (a flowing solid, gas or liquid). The invention is thus desirable for use in the testing and/or monitoring of ground-water, environmental air quality, and as alarm systems able to detect the accidental (or intentional) discharge of organic pollutants—indicated, for example by: pH value, metal ions, polyaromatic hydrocarbons, and volatile organic compounds.

Since the present invention is definable in multiple formats and may also be employed for a variety of divergent purposes and applications, the subject matter as a whole which is the present invention will be presented and described initially as component parts and then collectively as assembled apparatus in order that the prospective user may more quickly recognize and appreciate their major differences and distinctions in comparison to fiber optic apparatus and systems conventionally known.

I. THE ORGANIZATION, CONSTRUCTION, AND ASSEMBLY OF THE IMAGING FIBER

The unique imaging fiber of the present invention comprises two essential components. The first component is a preformed, unitary fiber optic array comprised of a plurality of individually clad fiber optical strands disposed co-axially along their lengths. The second component is a gradient index lens joined to and optically aligned with the unitary fiber optic array for far-field viewing of an object placed within a predetermined range of optical distances from the lens.

A. The Preformed Unitary Fiber Optic Array

The unique fiber optic array, its organization and construction, and its component parts are illustrated by FIGS. 1–5 respectively. Each discrete, unitary fiber optic array is a preformed bundle comprised of a plurality of individually clad, fiber optical strands disposed co-axially along their lengths and has a predetermined overall configuration and dimensions. The common repeating unit within the preformed array is thus a single optical fiber strand. The manner in which these optical fiber strands are prepared and the mode in which these prepared optical strands are joined collectively into an organized optic bundle of fibers is conventionally known, but are fundamental to a proper understanding and use of the alternative construction and format for the optic sensor.

Figure 2B:
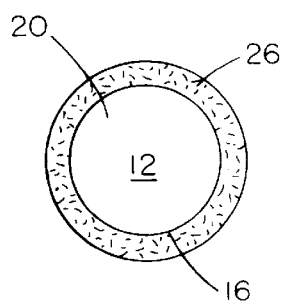
FIGS. 2A and 2B are views of the proximal and distal surfaces of the single core, optical fiber strand of FIG. 1.
Figure 2A:
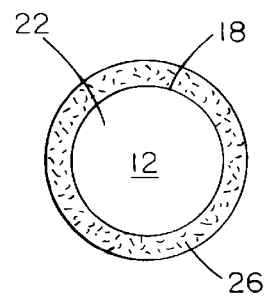

A typical single optical fiber strand is illustrated by FIGS. 1 and 2A and 2B. As seen therein, an individual optical fiber strand 10 is comprised of a single optical fiber core 12 having a rod-like shaft 14 and two fiber strand ends 16, 18, each of which provides a substantially planar end face surface. The intended "distal" surface 22 at the fiber end 18 is illustrated by FIG. 2A while the intended "proximal" surface 20 at the fiber end 16 is illustrated within FIG. 2B. It will be recognized and appreciated that the terms "proximal" and "distal" are relative and interchangeable until the strand is ultimately positioned in the array.

The optical fiber core 12 is composed typically of glass or plastic and is a flexible rod able to convey and transmit light energy introduced at either of its ends 16, 18. Such optical fibers 12 are conventionally known and commercially available. Accordingly, the optical fiber 12 is deemed to be conventionally known and available as such.

It will be appreciated that FIGS. 1–2 are illustrations in which the features have been purposely magnified and exaggerated beyond their normal scale in order to provide both clarity and extreme detail. Typically, the conventional optical fiber has a cross section diameter of 5–500 micrometers; and is routinely employed in lengths ranging between millimeters (in the laboratory) to kilometers (in field telecommunications). Moreover, although the optical fiber 12 is illustrated via FIGS. 1–2 as a cylindrical extended rod having substantially circular proximal end distal and surfaces, there is no requirement or demand that this specific configuration be maintained. To the contrary, the optical fiber may be polygonal or asymmetrically shaped along its length; provided special patterns and shapes at the proximal and/or distal faces; and need not present an end surface which is substantially planar. Nevertheless, for best efforts, it is presently believed that the substantially cylindrical rod-like optical fiber having planar end surfaces is most desirable.

Each optical fiber 12 is desirable, but not necessarily individually clad axially along its length by cladding 26. The presence of cladding is particularly desirable and important (a) to insure that light rays are totally internally reflected during their transmission; and (b) to minimize the "cross-talk" between individual optical fiber strands. This cladding 26 is composed of any material which is optically dense and prevents the transmission of light energy photons from the optical fiber 12 to the external environment. The cladding material 26 may thus be composed of a variety of radically different chemical formulations including various glasses, silicones, plastics, cloths, platings, and shielding matter of diverse chemical composition and formulation.

The manner in which the optical fiber core 12 is clad is also inconsequential and of no importance to the present invention. The conventional methods of deposition, extrusion, and covering are scientifically published and industrially available; and any of these known cladding processes may be chosen to meet the requirements and convenience of the user. Moreover, the quantity of cladding employed need be only that minimal amount which effectively prevents light energy conveyed by the optical fiber 12 from escaping into the ambient environment. It will be recognized and appreciated therefore, that the depth of cladding 26 as appears within FIGS. 1 and 2 respectively is greatly exaggerated and purposely thickened in appearance in order to show the general relationship; and is without scale or precise ratios between the cladding 26 and the optical fiber core 12.

It will also be recognized that the configuration of the cladding 26 as shown by FIGS. 1 and 2 has been shaped as a circular coating as a preferred embodiment only. For reasons as will become clear subsequently, it is desirable that the cladding 26 take form in regular geometric form as a round or oval shape. The illustrated configuration, however, is merely a preferred embodiment of the cladding 26 as it extends co-axially along the length of the optical fiber core 12. For purposes of added clarity also, FIG. 1 reveals the individually clad, optical fiber strand 10 in partial cross-section to demonstrate the relationship between the optical fiber core 12 and the cladding 26 which is coextensive along its axial length.

For general construction of the unitary fiber optic array and for most purposes and applications of the optical detecting system described hereinafter, it is desirable to employ the individually clad, fiber optical strand illustrated by FIGS. 1, 2A, 2B in preference to a bare strand. Clearly, the optical fiber strand 10 of FIG. 1 comprising a single-core optical fiber is unable to transmit light energy photons to any other optical fiber or strand due to the cladding material 26. This cladding, having a refractive index less than the strand core, prevents loss of light energy photons into the general environment. Accordingly, the potential for photon loss, distortion, or other optical error is minimized and reduced. Without the encompassing cladding, the bare optical fiber strand would allow the light energy photons to migrate partially from one fiber to other adjacently positioned fibers. This "cross-talk" phenomenon provides an undesirable risk of increasing the potential for quantum loss of light energy photons; for allowing aberrations of light energy wavelengths via the cross migrations of photons; and for permitting a greater range of reflection angles for distortion or loss of the light energy as it travels axially along the length of the fiber. For these reasons, the individually clad optical fiber mode of construction is preferable to the use of bare optical fiber strands in order to achieve greater precision and accuracy.

Figure 3:
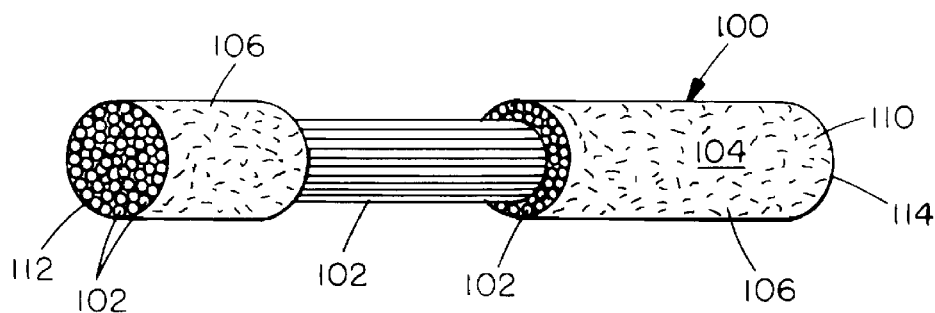
FIG. 3 is an overhead view of a preformed, unitary fiber optic array.
Figure 4:
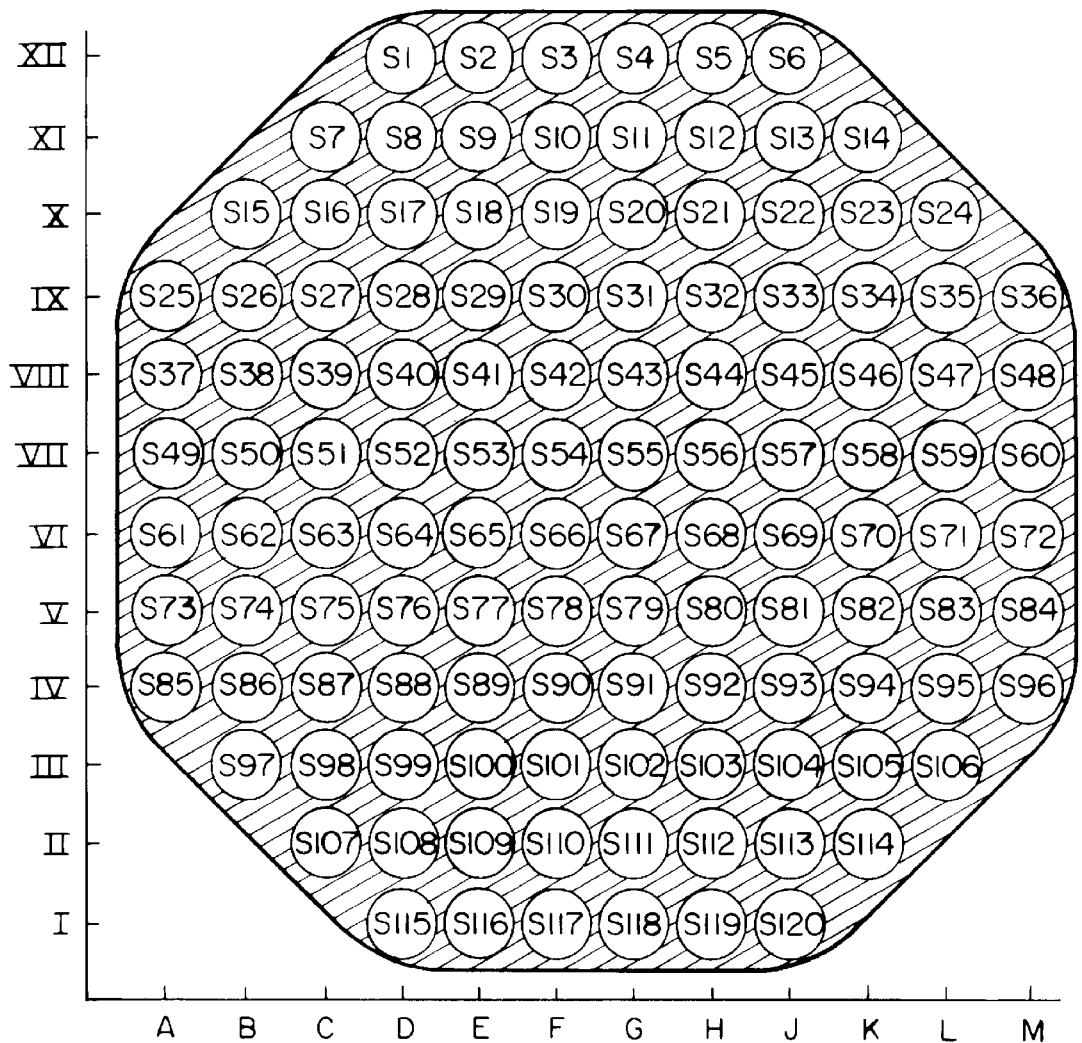
FIG. 4 is a view of the intended proximal array surface of the unitary fiber optic array of FIG. 3.
Figure 5:
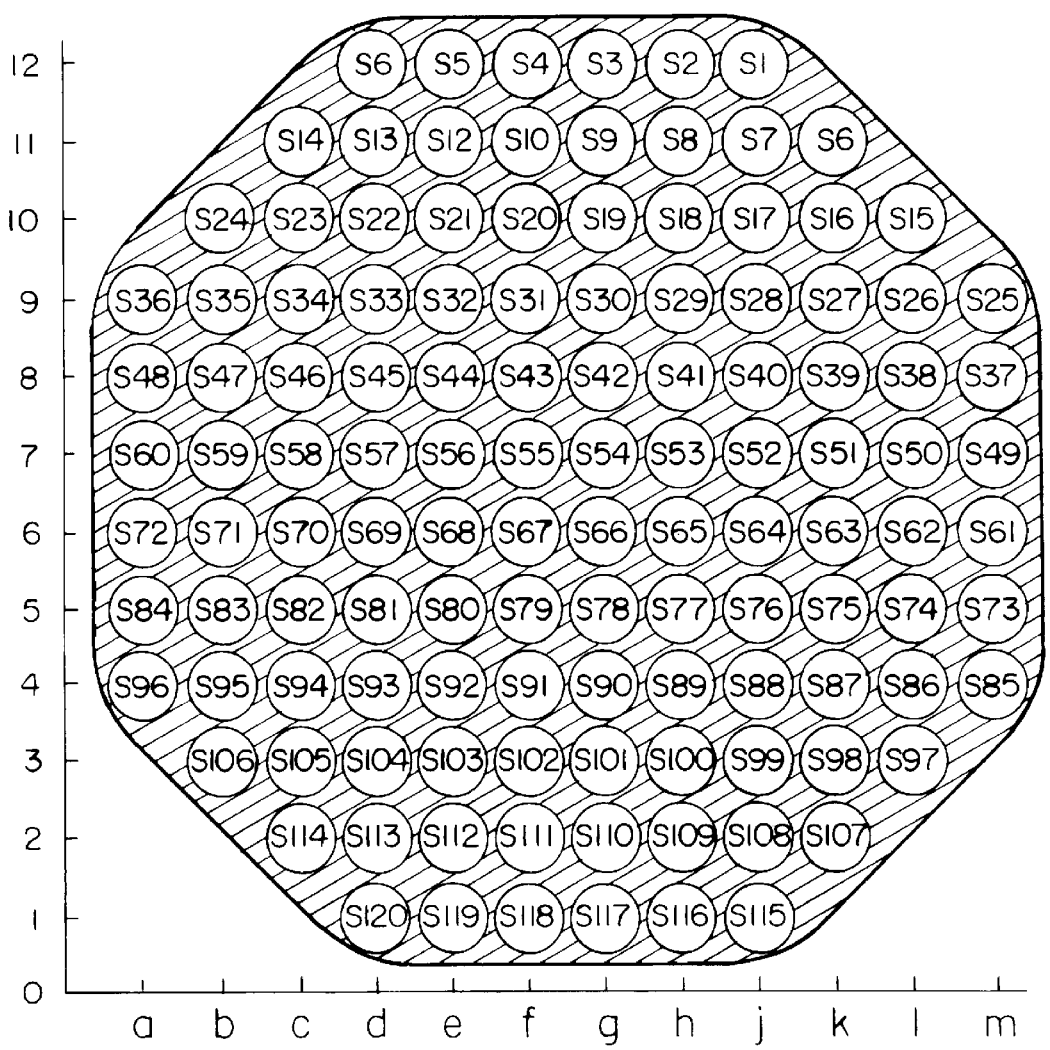
FIG. 5 is a view of the intended distal array surface of the unitary fiber optic array of FIG. 3.

A typical fiber optic array is illustrated by FIGS. 3–5 respectively. The unitary fiber optical array 100 appears in exaggerated, highly simplified views without regard to scale within FIG. 3. The preformed array is composed of a plurality of individually clad, fiber optical strands 102 which collectively lie co-axially along their respective lengths as the discrete unitary optic array 104 having a fixed and determinable configuration and set dimensions.

The construction organization and positional alignment within a typical fiber optical unitary array is revealed by FIGS. 3–5. For descriptive purposes only, each of the individually clad, optical fiber strands 102 is presumed to be linearly straight in position and has been arbitrarily assigned an identifying number S1–S120 as illustrated by FIGS. 4 and 5. The intended proximal optic array surface 112 of FIG. 4 shows that each of the individual fiber optical strands S1–S120 can be identified and distinguished from its adjacently disposed neighbor as well as from any other optical fiber strand within the preformed array 104 by a set of spatial positioning coordinate numbers for the strand end faces. The intended proximal optic array surface 112 may thus be arbitrarily divided into two axial directions as is illustrated by FIG. 4. The exact location of the S1 strand is thus identifiable by the numerical coordinates "XII D" showing the strand end face. Similarly, the exact spatial positioning and strand end face of the S71 fiber is designatable as "VII L". In this manner, the individual spatial position and strand end faces for each optical fiber strand S1–S120 is thus completely locatable and identifiable using the coordinate numeral labeling system.

The other optic array surface 114 (the intended distal surface) allows for a similar mode of identification (presuming straight linear alignment of strands) by spatial positioning of each individual optical strand—again as a result of dual-axis numerical coordinates as seen in FIG. 5. Accordingly, fiber and strand end face S1 is located at numerical position "12j", and fiber S71 is identifiable, locatable, and distinguishable from all other fibers at the optic array surface by its individual numeral coordinates "6b". In this manner, the precise and exact position of each individually clad optical fiber strand and strand end faces on each of the discrete optic array surfaces 112, 114 can be located, identified, and specified via a series of two different numerical coordinates. The intended proximal and distal optic array surfaces are thus completely identifiable and distinguishable as per individual fiber optical strand 102 despite its presence in the preformed collective body 106 of the unitary fiber optical array 100.

It will be recognized and appreciated also that the preformed overall organization of the individually clad, optical fiber strands 102 within the unitary array 100 is as aligned, parallel, strands which maintain its relative organizational positioning in a coherent, consistently straight manner over the entire length of the collective body 106. This is deemed to be the most desirable and most easily constructable organization scheme for the preformed optical fiber array of the present invention.

However, although this highly organized, coherent, and rigidly aligned collective construction is deemed to be most desirable, this high degree of organizational alignment is not an absolute requirement for each and every embodiment of the unitary optical array. Alternative manufacturing practices allow for a more random disposition of the individually clad, optical fiber strands disposed co-axially along their lengths. Although less desirable, a partially random disposition or a completely random alignment of the optical fiber strands will also result in a unitary collective body of optical fibers and in proximal and distal collective ends which provide two discrete optic array surfaces.

In such embodiments, however, an optical fiber strand 102 whose intended proximal end would be found to be at numerical position "11J" of FIG. 4 could randomly present an intended distal end position designated as "3e" within FIG. 5. It will be recognized therefore that while the individually clad, optical fiber strands lie adjacent one another along the entirety of their axial lengths—their position relative to one another, however, may vary in part or in whole, thereby creating a semi-coherent or an incoherent alignment which will vary in the degree of randomness to be found within their organizational construction. There is no requirement as such that the positioning of the intended proximal end of one strand be aligned and/or identical with the positioning of the intended distal end within the unitary optic array. Thus, in such randomly organized optical array constructions, therefore, the precise proximal and distal end positioning for the strand end faces would be measured and identified by passing light energy through individual optical fibers at one optic array end face and empirically determining the location of the light energy photons exiting from the other end of the same single fiber strand. Although far more laborious and inconvenient, by performing this extra step of empirically coordinating the proximal and distal ends of each individual optical fiber strand in the unitary array, an analogous exact set of numerical coordinates identifying the precise spatial positioning of the fiber at each end of the array may be obtained.

The entirety of the construction for the unitary imaging optical fiber array (whether uniformly coherent, semi-random, or completely randomly organized) provides a means of introducing light energy photons of any determinable wavelength at one specific position on one optic array surface; and then be able to predict accurately the spatial position of the light energy exiting at the other optic array surface. Therefore, by using the preferred completely coherent and rigidly maintained parallel alignment of strands illustrated FIGS. 4 and 5 (the intended proximal and distal optic array surfaces respectively) of a unitary fiber optic array, the user may introduce light energy to a specific spatial location on the "proximal" optic array surface 112—for example, only to fibers S1, S7 and S8—and have accurate knowledge and confidence that the light energy would be conveyed only by those three optical fiber strands and exit from numerical positions "12$j$", "11$j$", and "11$k$" alone on the "distal" optic array surface 114. No other light energy would appear from any other spatial position from the optic array surface 114. Similarly, were light energy of specific wavelengths introduced at the "proximal" optic array surface 112 via fibers S107, S108, and S115 respectively, the user can accurately predict and identify that the light energy will be conveyed by only these three optical fibers; and will exit only at the "distal" optic array surface 114 of numerical coordinate position numbers "2$k$", "2$j$" and "1$j$" respectively and from no other spatial positions on this optic array surface. In this manner, not only does one have knowledge of the individual spatial positioning of each optical fiber strand in the preformed array but also has the ability to identify and precisely locate light energy photons emerging from individual optical fiber strands within the whole of the optic array surface in a practical and reliable mode.

Accordingly, this fiber optic array construction allows for and provides the capability for the precise spatial positional introduction and conveyance of light energy via the different optical fiber strands with the collective body of the preformed, unitary fiber optic array. This capability to introduce or capture light energy photons at precise spatial positions at one optic array surface of a unitary array: to convey the introduced or captured light energy along the length of only a few specific optical fiber strands; and to control the exit of the conveyed light energy at a second, precisely known, spatial position on the other energy at a second, precisely known, spatial position on the other optic array surface of the unitary array is the hallmark of the fiber optic array construction format.

B. The Gradient Index ("GRIN") Lens

An essential component of the present invention is the presence of a Gradient Index or "GRIN" lens joined to and optically aligned with the distal optic array surface of a single optical fiber strand or of the unitary fiber optic array. GRIN lenses are conventionally known and currently employed to provide far-field focused viewing for optical fibers. A representative embodiment of a GRIN lens is illustrated by FIG. 6.

Figure 6:
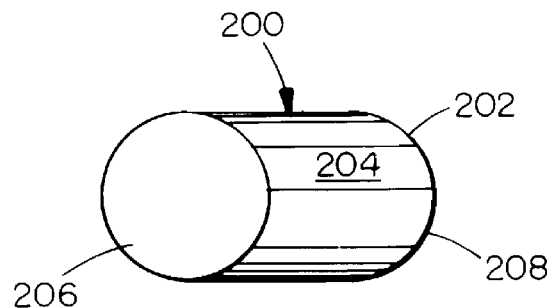
FIG. 6 is an overhead view of a gradient index lens.

As appears in FIG. 6, the GRIN lens 200 is a substantially cylinder-shaped rod 202 having a rounded lens body 204 and two substantially planar face ends 206 and 208 will conform to those of the unitary fiber optic array body and the intended distal optic array end chosen for that sensor construction. Moreover, the pitch, lens diameter, lens length, focal length, design wavelength, refractive index profile, axial index, and other GRIN lens parameters and capabilities may be individually chosen and varied to meet the specific demands of the user or the application as illustrated by the data of Tables 1 and 2 below—but the GRIN lens will typically take physical form as shown by FIG. 6.

Gradient Index or "GRIN" lenses typically are short (1–3 mm) small diameter glass rods that refract light. They are useful for direct attachment or coupling to optical fibers or detectors; and are commonly employed to couple light from one fiber to another. The refractive index of the material forming a GRIN lens varies radially, from a maximum on the axis to a minimum at the outer surface; and a refractive index profile is commonly provided for each GRIN lens to indicate its capabilities. In use, when a ray of light enters the GRIN lens at any angle, this light is continuously directed toward the center of the lens by the refractive index gradient. The path of the light ray forms a sinusoid. The period of the sinusoid is called the pitch, i.e., the length of rod required for one cycle; and the pitch determines the imaging distances for the lens. Different GRIN lenses provide a variety of different fractional pitches; and thus the distance for far-field viewing and imaging is preselected by the choice of the fractional pitch for the lens. The data provided by Tables 1 and 2 merely illustrate (by examples commercially sold) the profiles of a conventionally available range of GRIN lens.

A number of generally available scientific and commercial publications also provide a comprehensive description and complete detailed information regarding the workings, manufacture, and capabilities of GRIN lenses. These include the following, each of which is expressly incorporated by reference herein: Oriel Corporation, *Optics & Filters,* Vol. III; Hecht, *Optics,* 2nd edition, Addison-Wesley Publishing Co., 1987; Landis, et. al., *J. Appl. Spec.* 49: 547–555 (1995); Sakamoto, T., *Appl. Opt.* 31: 5184–5190 (1992); Landis et. al., *Appl. Opt.* 33: 3432–3439 (1994); von Bally et. al., *Appl Opt.* 26: 3425–3429 (1986); Gomez-Reino et. al., *Appl. Opt.* 25: 3418–3424 (1985); Harrigan, M. E., *Appl. Opt.* 23: 2702–2705 (1983); Harrigan, M. E., *Appl. Opt.* 27: 459–464 (1987); Rogers et. al., *Appl. Opt.* 27: 452–458 (1987); Acosta et. al., *Appl. Opt.* 26: 2952–2955 (1986); Acosta et. al., *Opt. Eng.* 28: 1168–1172 (19); Kitano et. al., *Appl. Opt.* 25: 3336–3339 (1985); and Palais, J. C., *Appl. Opt.* 19: 2011–2018 (1979).

Manufacturers can manipulate the GRIN lens parameters for varying optical, mechanical and working distance (i.e., the distance from the lens surface to the focal point of the object) requirements. Typically, the GRIN lens can be employed for wavelengths between 380 and 2000 nm with >89% transmission. However, transmission up to 99.5% can be achieved with an anti-reflective coating. A number of anti-reflective coatings are conventionally known and commercially sold in different grades. An illustrative listing of commercially sold anti-reflective coatings is provided by Table 3 below.

The value and benefit of anti-reflective ("AR") coatings is their ability to reduce the amount of light lost due to Fresnel reflections at the lens surfaces. AR coatings also help to protect the lens surfaces from humidity, chemical reaction and physical damage. This range and grades of AR coatings provide a broad range of characteristics; and the various coatings are typically optimized for specific wavelength(s) usages.

For GRIN lens generally, an acceptable working distance range is 3–8 mm with an optimal working distance of 5 mm (for a 0.35 mm×1.0 mm GRIN lens). Note also that at a working distance of 5 mm, the GRIN lens provides a 14× demagnification of the object. Consequently, a field of view 14-times the size of the imaging fiber can be imaged by coupling a GRIN lens to an imaging fiber.

To obtain an image with an optical imaging fiber, the fiber must be held in direct contact with the target. This limits the field of view to the size of the imaging fiber (e.g. 350 um i.d.) In contrast, by coupling a GRIN lens to an optical fiber, the field of view is expanded greatly. This occurs because the GRIN lens images the object from a remote plane and demagnifies it onto the optical surface of the fiber. Therefore, the object does not have to be in direct contact with the optical fiber-lens system. GRIN lenses can be therefore employed for light collimation and signal transmission with single-core fibers. Imaging GRIN lenses can also be used as an objective to gather light with unitary bundles of optical fibers.

Figure 7:
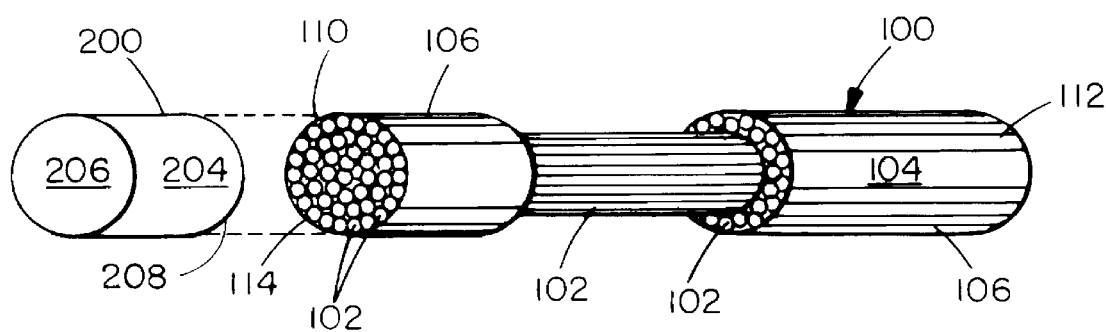
FIG. 7 is an exploded overhead view of a two-component imaging fiber embodying the components illustrated by FIG. 3 and FIG. 6 in the present invention.

The proper positioning of the GRIN lens can be achieved as shown by this exploded illustration of FIG. 7 in which the rod end 208 of a GRIN lens 200 is integrally joined and optically aligned with the distal optic array surface 114 of the unitary fiber optic array 100. In this alternative format, the GRIN lens body 204 is in intimate contact and is deposited upon the distal array end 110; and the rod front 206 of the GRIN lens optically positioned and aligned over the entire distal optic array surface 114 of the unitary fiber optic array 100. This also results in a two-component imaging fiber construction.

GRIN lenses provide a number of advantages for far-field viewing. The cylindrical shape of a GRIN lens is easily held and mounted to a unitary fiber optic array; the length of the GRIN lens can be chosen so that a real image is formed at the surface of the lens; and the GRIN lens can be joined to the fiber optic array directly with index matching epoxy, thereby minimizing throughput losses. The GRIN lens also provides a greater or larger field of view.

TABLE 1

ORIEL GRADIENT INDEX LENS TECHNICAL PROFILE*

| Fractional Pitch | Diam. (mm) | Length (mm) | Focal Length (mm) | BFL (mm) | Design Wavelength nm | N.A. | Axial Index (No.) | $\sqrt{\sqrt{A}}$ |
|---|---|---|---|---|---|---|---|---|
| 0.25 | 2.0 | 8.36 | 2.59 | 0 | 633 | 0.37 | 1.5837 | 0.247 |
|  | 2.0 | 5.46 | 2.64 | 0 | 830 | 0.37 | 1.5569 | 0.243 |
|  | 2.0 | 6.36 | 2.59 | 0 | 633 | 0.37 | 1.5637 | 0.247 |
|  | 2.0 | 6.46 | 2.64 | 0 | 830 | 0.37 | 1.5569 | 0.243 |
|  | 1.2 | 3.65 | 1.4 | 0 | 630 | 0.60 | 1.6578 | 0.430 |
|  | 1.8 | 3.71 | 1.44 | 0 | 830 | 0.60 | 1.6457 | 0.423 |
| 0.29 | 1.8 | 5.37 | 1.89 | −0.471 | 638 | 0.46 | 1.6075 | 0.339 |
|  | 1.8 | 5.49 | 1.95 | −0.484 | 830 | 0.46 | 1.5896 | 0.332 |
| 0.18 | 1.5 | 3.33 | 2.03 | 0.563 | 633 | 0.46 | 1.6075 | 0.339 |
|  | 1.8 | 3.41 | 2.08 | 0.887 | 630 | 0.46 | 1.5888 | 0.332 |

*ORIEL Gradient Index Lens Product Catalogue, 1992

TABLE 2

SELFOC IMAGING LENS TECHNICAL PROFILE

| Lens Type and Dia. (mm) | Lens Length Z (mm) | Resolution (LP/mm) Center | at 0.8R | Typical Chromatic Aberration ($\mu$m) | Typical $\sqrt{A}$ (mm$^{-1}$) | Magnification at WD = 5 mm | Field Curvative | View Angle (20) | Refractive Index ($N_O$) |
|---|---|---|---|---|---|---|---|---|---|
| ILW-0.25 | 0.70 +/− 0.10 | 400 | 150 | — | 2.319 | 19.1 | 40$\mu$ |  |  |
| ILW-0.35 | 0.96 +/− 0.10 | 300 | 120 | 49 | 1.710 | 14.1 | 40$\mu$ |  |  |
| ILW-0.50 | 1.39 +/− 0.13 | 250 | 100 | 51 | 1.203 | 9.9 | 50$\mu$ |  |  |
| ILW-0.70 | 2.00 +/− 0.20 | 200 | 80 | 82 | 0.856 | 7.1 | 60$\mu$ | 500 | 1.643 |
| ILW-1.00 | 2.95 +/− 0.30 | 200 | 50 | 102 | 0.600 | 5.1 | 80$\mu$ | min. | on axis |
| ILW-1.30 | 3.96 +/− 0.35 | 180 | 40 | 144 | 0.462 | 3.9 | 100$\mu$ |  |  |
| ILW-2.00 | 6.54 +/− 0.60 | 160 | 30 | 261 | 0.299 | 2.7 | 150$\mu$ |  |  |
| ILW-2.70 | 9.34 +/− 0.80 | 140 | 20 | 314 | 0.222 | 2.1 | 200$\mu$ |  |  |
| ILH-0.25 | 0.50 +/− 0.10 | 400 | 150 | — | 3.126 | 26.9 | 40$\mu$ |  |  |
| ILH-0.35 | 0.74 +/− 0.10 | 350 | 120 | 35 | 2.196 | 18.4 | 60$\mu$ | 700 | 1.666 |
| ILH-0.50 | 1.05 +/− 0.15 | 300 | 80 | 42 | 1.569 | 13.1 | 80$\mu$ | min. | Qnaxix |
| ILH-0.70 | 1.50 +/− 0.20 | 280 | 60 | 47 | 1.118 | 9.4 | 100$\mu$ |  |  |
| ILH-1.00 | 2.19 +/− 0.30 | 250 | 30 | 76 | 0.786 | 6.7 | 100$\mu$ |  |  |

*NSG America Inc. Product Guide, 1994

TABLE 3

SELFOC ANTI-REFLECTION COATINGS*

| ITEMS/COATING TYPE | NON-COATED | A-GRADE | C-GRADE | D-GRADE | W-GRADE |
|---|---|---|---|---|---|
| Maximum Total Reflection from Both Surfaces | 9–12% | 0.5% | 2.5% | 1.0% | 1.0% |
| Spectrum Width at at Maximum Reflectance | — | $\lambda$ +/− 15 nm | $\lambda$ +/− 30 nm | 830 +/− 15 nm 1300 +/− 30 nm | 1300 +/− 30 nm 1560 +/− 30 nm |
| Coating Surface | — | Multilayer Metal Oxide | Single Layer $MgF_2$ | Multilayer Metal Oxide | Multilayer Metal Oxide |
| Maximum Temperature | 350° C. | 200° C. × 1000 Hrs. | 200° C. × 1000 Hrs | 200° C. × 1000 Hrs | 200° C. × 1000 Hrs. |
| Maximum Humidity and Reliability | Not recommended for high humidity | 85° C.-85% RH 1000 Hrs. | 60° C.-95% RH 1000 Hrs. | 85° C.-85% RH 1000 Hrs. | 85° C.-85% RH 1000 Hrs. |

*NSG American Inc., Product Catalogue, 1994

C. A Preferred Assembly for the Constructed Imaging Fiber

Figure 8:
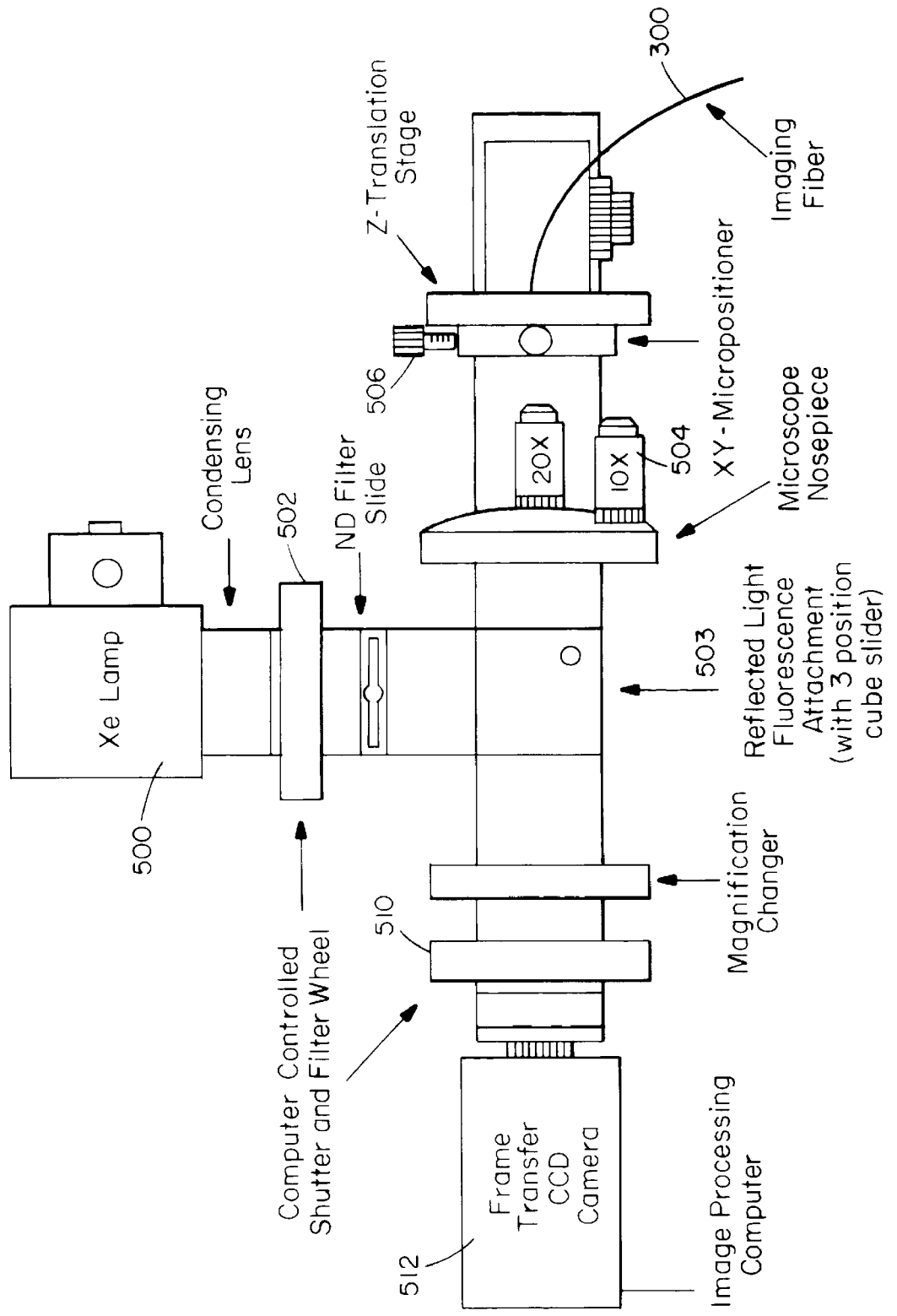
FIG. 8 is a schematic representation of an assembly suitable for concurrent viewing and chemical sensing using the sensor of FIG. 7.

Optical measurements and visual imaging performed using the assembly shown schematically in FIG. 8. White light from a 75 Watt, xenon arc lamp 500 was collimated; passed through an excitation filter 502; reflected by a dichroic mirror 503; and focused on the proximal end 112 of the far-field imaging fiber 300 with a 10× or 20× microscope objective 504 (Rolyn Optics). The far-field imaging fiber 300 (comprising the unitary fiber optic array and GRIN lens), is held in an xyz-micropositioner 506 (Spindler and Hoyer), which allows for fine focusing and precise positioning. Excitation light is transmitted from the imaging fiber's proximal face to the distal face where the excitation light illuminates the reaction surface of a remotely-situated solid substrate (not shown). The emerging light (typically fluorescent light) from the remotely-situated reaction surface is collected by the microscope objective 506; transmitted through the dichroic mirror 503; filtered at the appropriate wavelength by filter wheel 510; and detected by charge-coupled device ("CCD") camera 512. Continuous ratiometric measurements are obtained by monitoring the wavelength of the emerging light while switching between two excitation filters using the computer-controlled filter wheels and shutters.

The images and light wavelength measurements are made using a Peltier-cooled frame-transfer CCD camera. Desirably, the CCD cameras are connected to a Macintosh Quadra 950 that possessed a video graphics card and image processing software (such as IP Lab Version 2.5.5).

II. A REMOTELY-POSITIONED REACTION SUBSTRATE

An essential part of the optical sensor system for making analytical determinations and measurements requires the existence of a remotely-positioned solid substrate spaced apart from but aligned with and lying within the pre-determined range of optical distances from the far-field imaging fiber. The solid substrate lying remotely from the imaging fiber must provide at least one discrete reaction surface suitable for far-field viewing; and must provide at least one light energy absorbing dye indicator disposed and immobilized on the reaction surface of the remotely-positioned substrate. The solid substrate thus serves two individual functions and capacities:

(a) First it provides a specific location and field of view for the imaging fiber. Since the solid substrate is aligned to and lies within a pre-determined range of optical distances from the GRIN lens of the imaging fiber, the solid substrate reaction surface provides a clear image, and aligned and focused field of view, and a greatly increased and magnified area of sensing sites which is both accurate and reliably reproduced.

(b) The solid substrate must provide at least one (and preferably multiple) discrete surface(s) for the deposition and immobilization of one or more dye/polymer formulations as chemical sensing indicator zones as well as a discrete reaction surface for interaction between the disposed indicator substances and the analyte species of interest to be detected and measured.

A. The Range and Diversity of Suitable Solid Substrates

A wide and diverse range of materials are useful and desirable as solid substrates. The general requirements for the solid substrate are effectively:

(a) that the substrate material be durable and preferably malleable; (b) that the material be at least chemically quiescent and non-reactive with both all envisioned test samples and the dye/polymer indicator formulations disposed on the surface of the substrate itself; (c) that the substrate material be effectively unchanging in its dimensions and configuration after being fabricated; (d) and that the surface of the material provide sufficient surface area and reactivity access to the dye/polymer formulations as well as ease of physical access by the test sample itself.

The chemical composition of the solid substrate material may be organic or inorganic or any combination of these. Thus glass of any known or conventional formulation and chemically resistant metals and alloy blends are suitable for use. Other available materials include the many conventional plastics and polymers conventionally employed today including polystyrene or durable plastics which are non-reactive and durable over time. In addition, in particular applications such as clinical or biomedical settings, one or more biological coatings may be employed to both protect the material composition of the solid substrate as well as to provide for the elimination and/or control of intrinsic biological reactions which form an inherent part of the assay technique itself. Exemplifying the latter are coatings comprising collagen, fibronectin, albumin, heparin, polyethylene glycol, and other complex biological products which are known to inhibit or eliminate non-specific binding reactions.

The overall size, actual dimensions, and configuration of the solid substrate and reaction surface can be varied greatly to meet the individual user's personal choices or particular needs. Thus, the dimensions may vary from a very few micrometers to even inches and feet and the overall configuration may be regular or irregular, coherent or non-coherent, symmetrical or non-symmetrical, geometric or non-geometric; and either easily fabricated or reproducible only with great difficulty. It is required only that at least one solid substrate and one reaction surface be in existence; however, it is often desirable that many individual reaction surfaces be employed collectively and in combination.

Accordingly, the solid substrate may take form in the alternative in many commonly available modes such as: glass cover slips, plastic or glass Petri dishes; microtiter plates; volumes of polystyrene beads (being either smooth or non-smooth on the surface); sieves formed of metal, plastic, or polymeric compounds; screens or nettings formed of plastic or metal; and trays, plates, or rocks having wells or open cavities ranging in size and scale from nanometers to inches in diameter. All of these ranges, varieties, formats, in solid substrates are deemed to be within the scope of the present invention.

B. A Preferred Chamber for Far-Field Viewing and Analytical Measurement

It is envisioned that in many applications and test circumstances, it is desirable to provide a housing at the remote location where the test sample is to be found and evaluated. Such a prepared housing is entirely optional; however, if present, a housing provides advantages and convenience both for the test system and the operator.

The benefits and advantages provided by the optional housing include the following: (a) the housing serves as a permanent locale for the solid substrate material with the immobilized dye/polymer formulations deposited in the surface; (b) the solid substrate and reaction surface can be maintained in proper optical alignment and at a pre-set or fixed distance which lies within the pre-determined range of optical distances from the GRIN lens of the imaging fiber; (c) the housing serves as a reaction chamber and provides means for introducing the fluid test sample to be imaged and analytically measured to the reaction surface of the solid substrate under controlled conditions; (d) the housing provides the operator and user with means for not only ingress and egress of the test sample but also with means for controlling the speed, volume, and rate of contact between the fluid sample and the immobilized dye on the surface of the solid substrate.

Figure 9:
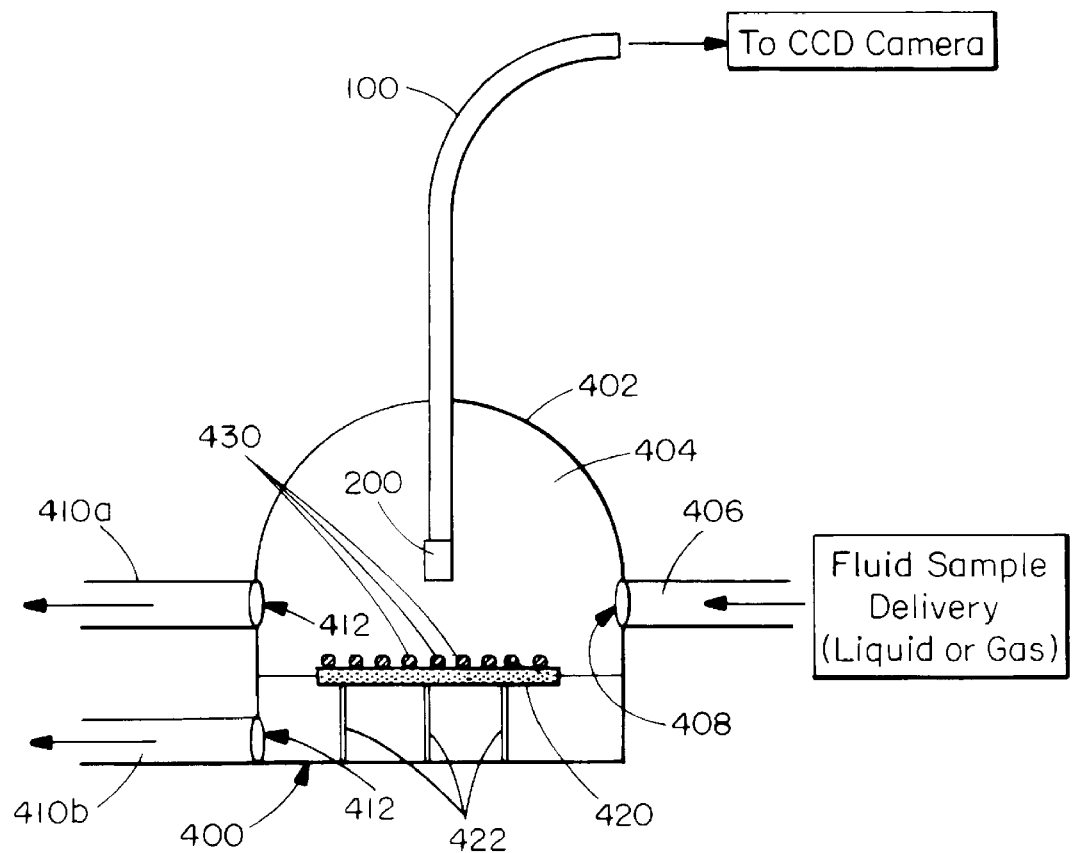
FIG. 9 is a view of a cassette cell housing for the solid substrate reaction surface and the indicator ligand provided chemical sensing zones.

Merely to provide ease of understanding and clarity of intended usage, an exemplary protective housing and reaction chamber is illustrated by FIG. 9. As shown therein, a protective housing 400 provides a protective shell 402 and an inner volume 404 for both far-field viewing and analytical measurements. The imaging fiber illustrated previously by FIG. 7 herein (comprising the unitary fiber optic array 100 and the GRIN lens 200) passes through the housing shell 402 into the interior volume 404 of the housing 400. Situated within a pre-determined distance from the GRIN lens 200 is a remotely-positioned substrate 420 which is maintained at a fixed optical distance from the fiber optic sensor by the supports 422. Disposed on the external surface of the solid substrate 420 are individual depositions of dye/polymer formulations 430 each disposed dye/polymer formulation reacting with at least one species of analyte when present in a fluid sample.

Ingress of the fluid sample (flowing solid, liquid, or gas) is provided by an entry duct 406 and the entry portal 408. The delivered fluid sample will flow over the reaction surface of the solid substrate 420 and react with at least some of the dye/polymer sensing zones 430 immobilized on the reaction surface. After reaction, the fluid sample is removed via discharge tubes 410a and 410b and exit portals 412. Discharge tube 410a generally provides for the exit and egress of gases lighter than air whereas discharge tube 410b will provide exit for liquid samples and gaseous samples heavier than air. The imaging fiber 300 comprising the fiber optic array 100 and the GRIN lens 200 is optically in communication with the assembly of FIG. 8 described previously herein; and thus both far-field viewing and optical analytical determinations and measurements are conducted repeatedly within the protective housing 400.

III. LIGHT-ENERGY ABSORBING INDICATOR FORMULATIONS

It is essential that at least one light-energy absorbing indicator ligand formulation be disposed upon a discrete reaction surface of the remotely-positioned solid substrate (with or without a housing). Note that the sole requirement for the indicator ligand formulation is that this substance generate and provide an optically detectable activity zone as such on the reaction surface of the solid substrate. Thus, not only dye compositions (fluorophoric and chromophoric) as such satisfy this requirement; but also moieties such as enzymes, antibodies, oligonucleotides, and dye precursor compounds (which only after specific reaction yield a fluorophore or chromophore)—are all distinct classes of different chemical compositions and are all individually, collectively, and cumulatively meet and satisfy the minimal requirement. Each of these classes and all its members are thus suitable for use as an indicator ligand formulation.

It will be therefore expressly recognized and understood that a wide and diverse range of many different chemical compositions are intended and envisioned for use in the present invention; and that among these many different and distinguishable classes of chemical compositions, light-energy absorbing dyes comprise only a single class—albeit a well characterized, highly favored, and frequently employed choice. For this reason, much of the detailed description which is presented hereinafter concerns itself with light-energy absorbing dye indicators. However, while such dyes are the most desirable choice, these dye indicators are merely one exemplary instance of preferred usage.

A. Fluorophoric and Chromophoric Dyes

The dyes which may be individually and collectively be employed and disposed for analytical measurements and optical determinations in combination with the assembled fiber optic sensor are all conventionally known and usually commercially available. The present invention intends that all the commonly useful properties and capabilities of the various classes of light energy absorbing dyes be employed as needed or desired for the specific use or application. Merely illustrative of the many different dyes are those fluorophores, fluorescent enzyme substrates, fluorescent antibody conjugates, and chromophores listed below within Tables 4 and 5 respectively.

TABLE 4

| Compounds | Excitation Wavelength (range or maximum) | Fluorescence emission range (max) |
|---|---|---|
| A. Fluorophores | | |
| Eosin | 520–530 nm | 530–580 nm (550 nm) |
| TRITC-amine | 555 nm | 570–610 nm (590 nm) |
| Quinine | 330–352 nm | 382–450 nm |
| Fluorescein W | 488–496 nm | 530 nm |
| Acridine yellow | 464 nm | 500 nm |
| Lissamine Rhodamine B Sulfonyl Chloride | 567 nm | 580 nm |

TABLE 4-continued

| Compounds | Excitation Wavelength (range or maximum) | Fluorescence emission range (max) |
|---|---|---|
| Erythroscein | 504 nm | 560 nm |
| Ruthenium (tris, bipyridium) | 460 nm | 580 nm |
| Texas Red Sulfonyl Chloride | 596 nm | 615 nm |
| B-phycoerythrin | 545, 565 nm | 575 nm |
| Nicotinamide adenine dinucleotide (NADH) | 340 nm | 435 nm |
| Flavin adenine dinucleotide (FAD) | 450 nm | 530 nm |
| Carboxy Seminaphthorhodafluor | 587 nm | 640 nm |
| Naphthofluorescein | 594 nm | 663 nm |
| B. Fluorescent Enzyme Substrates | | |
| Fluorescein mono-B-D-galacto-pyranoside | 452 nm | 518 nm |
| Resorufin B-d-glucuronide | 468 nm | 584 nm |
| 8-acetoxypyrene -1,3,6-trisulfonic acid trisodium salt | 368 nm | 391 nm |
| Coenzyme A (1-pyrene butanoic acid) ester | 339 nm | 377 nm |
| Fluo-3; free acid [Molecular Probes, Eugene, CA] | 506 nm | 526 nm |
| Quin-2, tetrapotassium | 352 nm | 492 nm |
| C. Fluorescent Antibody Conjugates | | |
| Texas Red goat anti-mouse Fg G conjugates | 590 nm | 615 nm |
| Protein A fluorescein conjugates | 480 nm | 520 nm |
| Anti-Atrazine fluorescein Conjugates | 480 nm | 520 nm |
| Apti-digoxin Texas Red Conjugates | 590 nm | 615 nm |

TABLE 5

| Chromophores | Range (max) |
|---|---|
| Iron-salicylate complex | 530 nm |
| Indamine dye | 590 nm |
| INT formazon dye | |
| Hopkins-Cole dye | 560 nm |
| Quinone-imine dye | 500 nm |
| Fe (SCN)$^{+2}$ | 460 nm |
| Malachite Green | 620 nm |
| 4-bromo A-231 87, free acid | 340 nm |
| Cresol red | 415 nm, acid; 570 nm, base |
| diphenylcarbazone disulphonic acid | 575 nm |
| Chrome bordeaux B | 575 nm |
| Calmagite | 650 nm |
| Ninhydrin dye | 650 nm |

It will be recognized and appreciated also that the range, variety, and diversity of light energy absorbing dyes, dye formulations, and dye mixtures suitable for use as indicators herein are not dependent upon a single light source or light energy supply in order to be effective. Although light energy of determinable wavelengths is desirably provided by electrical light sources—that is, light emitting diodes (LED's), lasers, laser diodes and filament lamps whose bands of light energy are typically controlled and selected by filters, diffraction gratings, polarizing filters or alternatively broken into various broad wavelengths of light energy via prisms, lenses, dichroics, or other optical/spectral articles, these are not exclusively the only sources of useful light energy. Clearly, in various applications and circumstances chemical light energy, bioluminescence, and other less typical or conventionally employed light energy sources are deemed to also be useful. Accordingly, neither the true source, nor the nature of light energy photons, nor the manner in which they are conveyed or otherwise caused to be created is of importance or consequence.

In addition, the dye individually may comprise other materials such as enzymes, antibodies, or chemical compounds for photoreactive contact. Thus each dye individually disposed on the solid substrate may in fact be formulated as a mixture of both light emitting and light absorbing dyes; and also comprise a variety of other light energy sensitive compounds made conventionally which are able to interact with specific dye properties. Merely exemplifying the nature of such multiple dye formulations and combinations are those described and claimed within copending U.S. Pat. No. 5,114,864 issued May 19, 1992 as well as the compositions described within U.S. Pat. No. 4,822,746 issued Apr. 18, 1989—the texts of which are individually expressly incorporated by reference herein.

B. A Completely Specific or Semi-Selective Dye Formulation

The present optical apparatus for far-field viewing and analytical measurements envisions and intends that either a completely specific reaction between a species of analyte and the dye indicator formulations occur; or, alternatively, that a plurality of semi-selective reactions occur between each dye indicator formulation and multiple species of analytes. The choice of generating a completely specific reaction or a semi-selective reaction which provides an optically detectable activity zone is left to the manufacturer or user to meet individual circumstances and/or particular applications.

A Completely Specific Dye Indicator Formulation Reacting Only with a Single Species of Analyte In one mode of use, only specific dye indicator reagents and formulations will be disposed on the reaction surface of the solid substrate. Thus, each immobilized light energy absorbing dye formulation or composition will react with only one species of ligand or one analyte of interest. Moreover, the dye indicator will then show evidence of such specific and selective reactive contact with one analyte by either absorbing and reflecting a portion of the light energy; or, alternatively, by absorbing light energy and then subsequently emitting light energy of a different wavelength in return. Such reflected or emitted light energy will be received and conveyed by the GRIN lens positioned over the distal optic surface of a unitary optic array; and such conveyed light will emerge from the proximal optic surface of the imaging fiber for detection and measurement.

The interactions between the light energy conveyed and the properties of the specifically binding, light absorbing dye—in the presence of one analyte of interest and as well as in the absence of any analyte species whatsoever—provide an optical basis for both qualitative and quantitative determinations. This traditional approach has therefore been to create highly selective sensors by finding and using specific binding dye materials; and this overall approach consequently results in creating one specific and selective dye reagent for each analyte or ligand of interest to be detected. The one analyte/one specific dye reagent approach thus has been used previously and remains today the overriding guiding principle and axiom for most optical chemical sensors and optical chemical sensing apparatus.

It is useful to recognize and appreciate the stringent demands and essential requirements of the traditional one analyte/one dye reagent approach. These include: (1) each optical detection apparatus must employ and use one highly selective/specific binding agent for binding and reaction with a single analyte or ligand of interest in a sample; (2) the sensor optical detection apparatus relies and depends upon the energy signal generated by the selective binding agent as the means for detecting and determining the presence of the single analyte or ligand in the sample; (3) the approach requires that for detection of multiple species of analytes of differing ligands, a series of different but individually selective dye reagents with separate and different binding specificities are used together as multiples concurrently or in sequence; and (4) the specific binding and signal generation of the optical detection apparatus be accomplished using a variety of different but completely selective dye reagents including calorimetric or fluorescent dyes and selective polymer films. In each instance, one specific dye formulation must be created for the detection of each species of analyte or ligand of interest.

Multiple Semi-Selective Dye Indicator Formulations Each Reacting with a Plurality of Different Analyte Species An alternative approach to making optical determinations and analytical measurements utilizes different and multiple dye indicator formulations concurrently, at least some dye indicator formulation reacting semi-selectively with the same species of analyte or ligand. The optical detection and measurement is made on the basis of spectral response patterns generated by the semi-selective, chemical sensing dye reagents. Each formulation of dye and polymer semi-selectively reacts with a plurality of different chemical compounds and compositions; and for each semi-selective reaction with an individual chemical compound, provides a spectral response pattern over time (by changes in energy intensity, or by changes in wavelength or both of these parameters) which is indicative of the event and consequence of the semi-selective reaction with species of analyte.

The plurality of semi-selective dye reagents immobilized on the reaction surface of the solid substrate will thus generate multiple optical signals over time which cumulatively and collectively form a spectral recognition pattern which is indicative and recognizable as a spectral pattern indicative of the presence of any analyte or ligand; and is the distinctive representational total of all the spectral responses from each of the different dye reagents immobilized on the substrate. For detection and evaluation purposes, the spectral recognition pattern would be stored in the retained memory of a computerized instrumentation system; and this spectral recognition pattern showing the response progressions serves as the spectral baseline and means for evaluation, as well as for recognizing, and identifying the presence or absence of an analyte or ligand in the testing system.

The use and apparatus for making optical determinations for the detection and measurement of at least one species of analyte using spectral recognition patterns and multiple semi-selective dye reagents in combination is disclosed in great detail within U.S. patent application Ser. No. 08/289,001 filed Aug. 11, 1994—the text of which is expressly incorporated by reference herein. Nevertheless, for purposes of the present invention, the manufacturer and/or ultimate user can immobilize and deposit a wide range and variety of different semi-selective dye indicator formulations and dye reagents on the reaction surface of the solid substrate. This discrete alternative format and mode of using semi-selective dyes provides both flexibility and meaningful choices for the optical apparatus in a degree not previously envisioned or possible before.

C. Disposition of Dye Indicator Formulations

Multiple methods of dye indicator disposition and immobilization are conventionally known. Thus, one may prepare a specific fluorescent indicator or colorimetric formulation comprising one or more dyes as well as other chemical compounds; and dispose the dye formulation either randomly over the entire surface or at a specific spatial position and location on the reaction surface of the solid substrate. Among the conventional practices of dye deposition and immobilization, a variety of polymerization processes are known including thermal techniques, ionization methods, plasma methods, and electroinitiation procedures. These different methodologies are exemplified by the following publications, the text of each being expressly incorporated by reference herein. Thermal methods: Graham et. al., *J. Org. Chem.* 44: 907 (1979); Stickler, M. and G. Meyeroff, *Makromal. Chem.* 179: 2729 (1978); and Brand et. al., *Makromol. Chem.* 181: 913 (1980). Ionization methods: A. Chapiro, *Radiation Chemistry of Polymer Systems,* Chapter IV, Wiley - Intersciences, Inc., New York, 1962; J. E. Wilson, *Radiation Chemistry of Monomers, Polymers, and Plastics,* chapters 1–5, Marcel Dekker, New York, 1974. Plasma Methods: Yasuda, W. and T. S. Hsu, *J. Polym. Sci. Polym., Chem. Ed.* 15: 81 (1977); Tibbett et. al., *Macromolecules* 10: 647 (1977). Electroinitiation methods: Pistoria, G. and O. Bagnarelli, *J. Polym. Sci.* Polym, *Chem. Ed.* 17: 1001 (1979); and Philips et. al., *J. Polym. Sci. Polym. Chem. Ed.* 15: 1563 (1977).

The preferred method of dye indicator disposition and immobilization for the present invention is via the process known as photoactivation; and employs one or more photoactivated monomer preparations in admixture with one or more pre-chosen light energy absorbing dyes as a photopolymerizable formulation. Such monomer preparations typically comprise solutions of several monomers in admixture and a concentration of at least one light energy absorbing dye conjugated to an organic carrier which can be chemically cross-linked. A representative listing of different monomer compositions suitable for preparing an admixture which subsequently can be photopolymerized are given by Table 6; and an illustrative listing of conjugated dyes ready for admixture and photopolymerization is given by Table 7 below.

TABLE 6

| | |
|---|---:|
| A. Monomers | |
| acrylamide | |
| N,N-methylene bis (acrylamide) | |
| hydroxyethylmethacrylate | |
| styrene | |
| vinylacetate | |
| (N-(3-aminopropyl) meth-acrylamide | |
| hydrochloride [Kodak, Inc.] | |
| B. Comonomer with | |
| dimethylsiloxane | |
| (acryloxypropy) methyl | (15–20%) |
| (aminopropyl) methyl | (3–5%) |
| (methacryloxypropyl) methyl | (2–3%) |
| C. T-structure | |
| Dolydimethylsiloxanes | |
| methacryloxypropyl | (25–50%) |
| vinyl | 50–75%) |

TABLE 7

Conjugated Dyes
acryloyl fluorescein
acryloyl rhodamine
acryloyl eosin
phenol red
acryloyl
8-hydroxypyrene
1,3 disulfonic acid
acryloyl
seminaphthorhodafluor
acryloyl
seminaphthofluorescein It will be appreciated that the listings of Table 4 and Table 5 are merely representative of the many different substances which can be usefully employed in admixture with one or more light energy absorbing dyes. In addition, the scientific and industrial literature provides many alternative monomer preparations and admixtures which are also suitable for use in making the present invention. Accordingly, all of these conventionally known monomer preparations are considered to be within the scope of the present invention.

IV. EXPERIMENTS AND EMPIRICAL DATA USING THE OPTICAL APPARATUS

To demonstrate the utility and effectiveness of the optical apparatus comprising the invention as a fully constructed exemplary system, a series of experiments and empirical data will be presented. It will be expressly understood, however, that the experimental details which follow hereinafter are merely illustrative and representative of the many different and alternative embodiments of the present invention which can be made to detect and accurately measure one or more species of analyte by optical determinations. There is, therefore, no restriction or limitation of the present invention to merely the aliquote choices, the listed regents, the individual light wavelengths utilized, the indicator ligands employed, or the substrate materials as disclosed hereinafter.

The experiments employ the preferred system and assembly illustrated by FIG. 8 and described in detail previously herein. The same apparatus was employed for both far-field viewing and imaging of objects as well as for making fluorescence measurements. For far-field viewing, white light is used for viewing and image collection. Alternatively, for fluorescence measurements, fluorescence is monitored as light energy emissions at specified wavelengths emerging from the dye indicators after the introduction of excitation light energy. The resulting data are digitized and analyzed by a Macintosh quadra 950 instrument and displayed on a screen.

Experimental Series 1

Figure 10:
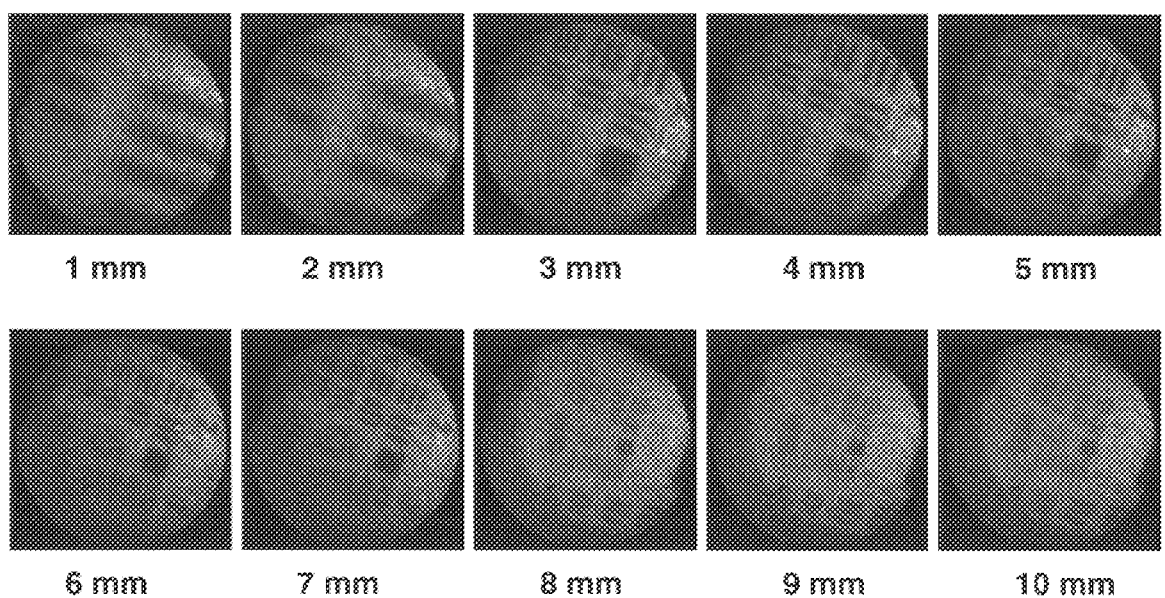
FIG. 10 is a series of photographs showing the viewing image obtained of an airforce resolution target over optical distances ranging from 1–10 millimeters remote from the fiber optic sensor of the present invention.

Initially, the far-field visual imaging capabilities of the optic apparatus are demonstrated by viewing a standard Air Force Resolution Target (Newport) using a unitary fiber optic array imaging fiber coupled to a 0.35×1.0 mm Selfoc imaging GRIN lens. The imaging capabilities, and spatial resolution for 1–10 millimeter working optical distances are illustrated by the white light images of FIG. 10. It will be recognized that each working optical distances from 1 millimeter up to 10 millimeters provides a greatly expanded field of view and focused image of the target. The optimum working distance from the GRIN lens of the imaging fiber is deemed to be 5 millimeters which provides both a clear image and a magnified field of view for the lines and pattern comprising the target itself.

Experimental Series 2

Example A

Indicator Ligand Preparation: Acryloylfluorescein (as an exemplary dye indicator) was prepared by mixing dry acetone (20 ml); fluoresceinamine isomer I (180 mg, 0.518 mmol); acryloyl chloride (45 µl, 0.55 mmol); and then allowing the reaction mixture to stir for 1 hour in the dark. The precipitate formed by the reaction was then filtered and washed with acetone, followed by addition of dichloromethane (volume not critical).

HEMA/Acryloylfluorescein/Ammonium persulfate polymerization solution: A stock solution was prepared formulated of 5 ml hydroxyethyl methacrylate (ophthalmic grade); 5 ml 0.1M phosphate buffer pH 6.8; 100 µl ethyleneglycol dimethacrylate (EGDMA); and 0.5 ml of dye solution (50 mg acryloylfluorescein in 100 ml propanol).

Polymerization Conditions: 1 ml of the stock polymerization solution is added to a 3 ml vial and deoxygenated by bubbling with $N_2$ for 15 minutes. The vial is set in a 55° C. water bath, at which time 1 mg ammonium persulfate is added, and the solid substrate (such as polystyrene beads ranging from 1–3 mm in diameter) are inserted. Polymerization of the mixture onto the external surface of the polystyrene is allowed to occur with constant stirring under $N_2$. The coated solid substrate is preferably removed just prior to reaction completion—as determined by a significant increase in viscosity. Polymerization times vary from batch to batch and from differences in the material of the solid substrate. Typically, polymerization and formation of the thin film is complete within 10 minutes.

Example B

Figure 11:
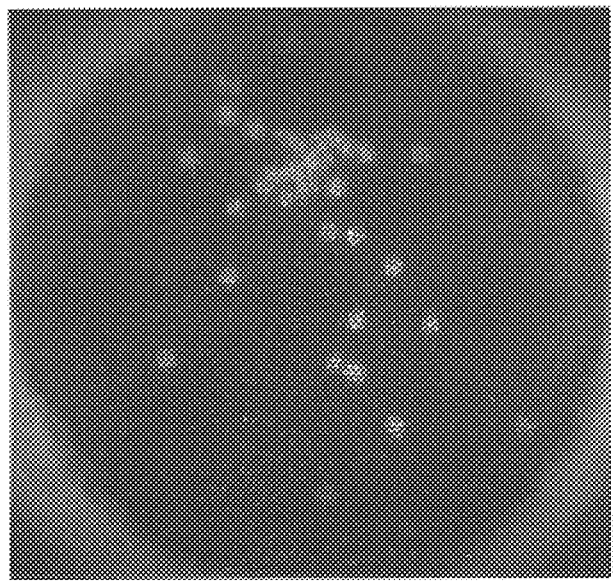
FIG. 11 is a photograph showing the fluorescent image of fluorescein-coated polystyrene beads at a distance of ~1 cm and at a magnification of 20×.

Initially, 80 micrometer size polyethylene glycol ("PEG") polystyrene beads were coated with fluorescein as described herein. This technique uses ionic binding of the dye indicator (fluoresein) to PEG-polystyrene beads. Initially the PEG-polystyrene beads are placed in the wells of a microtiter plate and soaked in a fluorescein dye solution. Distilled water is then added to each well and the beads vortexed. The water is then removed and the beads are washed once with fresh distilled water. After rinsing, the fluorescein-coated beads are placed in distilled water and viewed using the imaging fiber and optical apparatus of the present invention. The result is shown by FIG. 11 which shows clear fluorescent images of the coated polystyrene beads remotely located ~1 cm distant from the GRIN lens of the imaging fiber.

Example C

Figure 12:
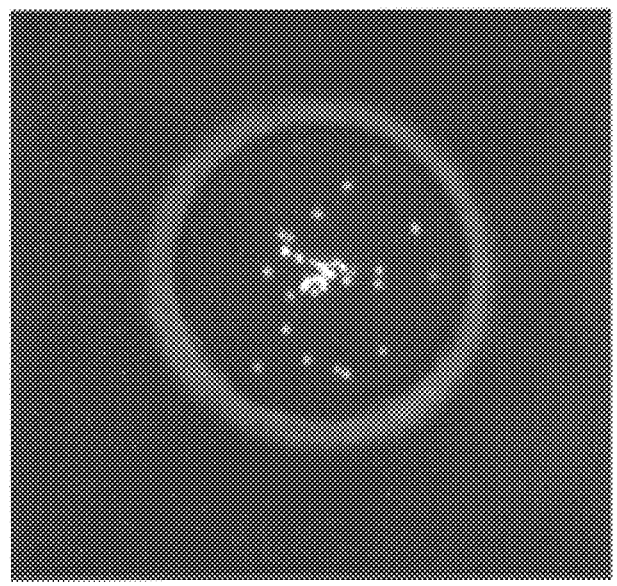
FIG. 12 is a photograph showing the fluorescent image of fluorescein-coated polystyrene beads at a distance of ~2 cm and at a magnification of 10×.

When the fluorescein-coated polystyrene beads of Example B are placed at ~2 cm optical distance from the imaging fiber of the optic sensor, a different overall remote image and far-field of view provided as illustrated by FIG. 12. The magnification has been reduced in comparison to the image of FIG. 11; and the far-field view is smaller in scale but provides a greater overall quantum of information over the entire reaction surface of the solid substrate.

Example D

Figure 13:
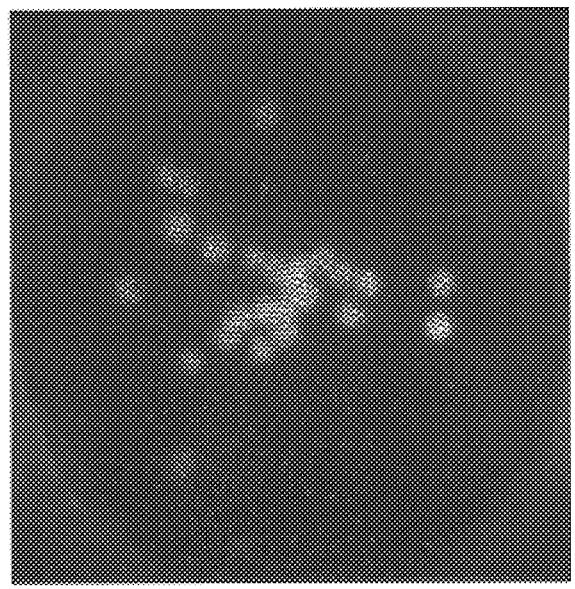
FIG. 13 is a photograph showing the fluorescent image of fluorescein-coated polystyrene beads at a distance of ~5 mm and at a magnification of 20×.

In contrast, an increased magnification and greater scale of far-field view for the fluorescent-coated polystyrene beads of Example B is provided by FIG. 13, which was acquired after decreasing the optical distance between the beads and the imaging fiber of the sensor to a distance of about 5 mm. By decreasing the optical distance between the beads and the imaging fiber, the field of view is also reduced; nevertheless, the decreased distance does allow for an increase in the collection of the fluorescent light energy emerging from the beads (after introduction of excitation light).

It is also useful to compare FIG. 13 with FIG. 11. Both of these show an image at a magnification of 20×; however, the optical distance of the image of FIG. 11 was about 10 mm while the image of FIG. 13 was only at about 5 mm distance.

Example E

Figure 14:
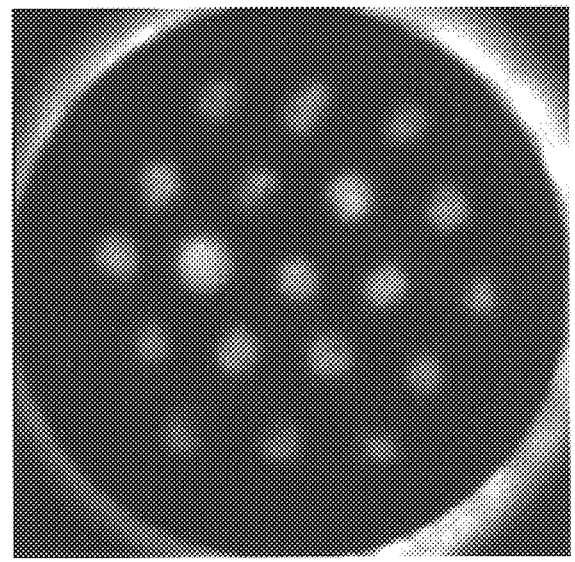
FIG. 14 is a photograph showing a fluorescent image of dye/polymer indicator filled wells in a glass substrate.

FIG. 14 illustrates an alternative solid substrate and reaction surface. The solid substrate is a glass microscope slide having 1 mm by 50 μm etched wells in a pre-arranged pattern; and the fluorescein-polymer filled wells are clear images, despite being remotely-positioned as fluorescent light images collected by the optical sensor of the present invention.

The invention is not to be restricted in form nor limited in scope except by the claims appended hereto.

What we claim is:

1. An optical sensor apparatus for far-field viewing and detection of at least one species of analyte in a remotely-position fluid sample, the detection of a species of analyte being correlatable with far-field optical determination, said optical sensor apparatus comprising:
    a far-field imaging fiber comprised of
        (a) a preformed, unitary fiber optic array comprising a plurality of individually clad, fiber optical stands disposed co-axially along their lengths and being of predetermined configuration and dimensions, said preformed unitary fiber optic array having two discrete optic array ends each of which is formed of multiple strand end faces and presents a discrete optic array surface for introduction and conveyance of light energy, and
        (b) a gradient index lens joined to and optically aligned with an optic array end surface of said unitary fiber optic array for far-field viewing of an object located within a predetermined range of optical distances from said lens;
    a remotely-positioned solid substrate spaced apart from but lying within said predetermined range of optical distances from said imaging fiber, said solid substrate providing, at least one discrete reaction surface in alignment with and suitable for far-field viewing via said imaging fiber,
    at least one light energy absorbing indicator ligand disposed on said discrete reaction surface of said remotely-positioned solid substrate, said indicator ligand providing a characteristic detectable optical response of time-varying light intensity at at least one wavelength, said response being indicative of an individual species of analyte when present in a fluid sample;
    means for placing a fluid sample into reactive contact with said light energy absorbing indicator ligand on said reaction surface of said remotely-positioned solid substrate;
    means for introducing excitation light energy to said light energy absorbing indicator ligand on said reaction surface of said remotely-positioned solid substrate; and
    means for detecting light energy emerging from said indicator ligand on said reaction surface of said remotely-positioned solid substrate which has been introduced and collected by said imaging fiber, said detected emerging light energy serving as a measure for determining a species of analyte in the fluid sample.

2. An optical sensor apparatus for far-field viewing and detection of multiple species of analyte in a remotely-positioned fluid sample, the detection of a species of analyte being correlatable with an individual far-field optical determination, said optical sensor apparatus comprising:
    a far-field imaging fiber comprised of
        (a) a preformed, unitary fiber optic array comprising a plurality of individually clad, fiber optical strands disposed co-axially along their lengths and being of predetermined configuration and dimensions, said preformed unitary fiber optic array having two discrete optic array ends each of which is formed of multiple strand end faces and presents a discrete optic array surface for introduction and conveyance of light energy, and
        (b) a gradient index lens joined to and optically aligned with an optic array end of said unitary fiber optic array for far-field viewing of an object located within a predetermined range of optical distances from said lens;
    a remotely-positioned solid substrate spaced apart from but lying with said predetermined range of optical distances from said imaging fiber, said solid substrate providing at least one discrete reaction surface in alignment with and suitable for far-field viewing via said imaging fiber;
    at plurality of light energy absorbing indicator ligands disposed individually at different spatial locations on said discrete reaction surface of said remotely-positioned solid substrate, at least one of said indicator ligands providing a characteristic detectable optical response of time-varying light intensity at at least one wavelength, said response being indicative of an individual species of analyte when present in a fluid sample;
    means for placing a fluid sample into reactive contact with said plurality of light energy absorbing indicator ligands on said reaction surface of said remotely-positioned solid substrate;
    means for introducing excitation light energy of predetermined wavelength to at least one of said light energy absorbing indicator ligands on said reaction surface of said remotely-positioned solid substrate; and
    means for detecting light energy emerging individually from at least one of said indicator ligands on said reaction surface of said remotely-positioned solid substrate which has been introduced to and collected by said imaging fiber, each detected emerging light energy serving as a measure for determining the presence of one species of analyte in the fluid sample.

3. The optical sensor apparatus as recited in claim 1 or 2 wherein said gradient index lens further comprises an anti-reflective coating.

4. The optical sensor apparatus as recited in claim 1 or 2 wherein said indicator ligand comprises a fluorophoric dye.

5. The optical sensor apparatus as recited in claim 1 or 2 wherein said indicator ligand comprises a chromophoric dye.

6. The optical sensor apparatus as recited in claim 1 or 2 wherein said indicator ligand comprises a moiety selected from the group consisting enzymes, antibodies, oligonucleotides, fluorescent precursor compositions, and chromophore precursor compositions.

7. The optical sensor apparatus as recited in claim 1 or 2 wherein said solid substrate further comprises a plurality of different reaction surfaces.

8. The optical sensor apparatus as recited in claim 1 or 2 wherein said solid substrate further comprises a housing.

9. The optical sensor apparatus as recited in claim 1 or 2 further comprises ingress means for delivering a fluid sample to said reaction surface of said solid substrate.

10. The optical sensor apparatus as recited in claim 1 or 2 further comprises egress means for removing a fluid sample from said reaction surface of said solid substrate.

11. The optical sensor apparatus as recited in claim 1 or 2 wherein said solid substrate takes form as an entity selected from the group consisting of a multiwell plate, a bead, a sieve, a screen, a netting, a multiwell tray, a multiwell rack, a dish, and a cover slip.

12. The optical sensor apparatus as recited in claim 1 or 2 wherein said reaction surface of said solid substrate comprises a coating material for inhibiting undesirable chemical or biological reactions.

* * * * *